US009604025B2

(12) United States Patent
Pastoor et al.

(10) Patent No.: US 9,604,025 B2
(45) Date of Patent: Mar. 28, 2017

(54) PATIENT INTERFACE ASSEMBLY WITH IMPROVED STABILIZATION

(75) Inventors: Sander Theodoor Pastoor, Eindhoven (NL); Krijn Frederik Bustraan, Eindhoven (NL); Tom Jan Severijn, Eindhoven (NL); Adrianus Johannes Josephus Van Der Horst, Eindhoven (NL); Jerome Matula, Jr., Apollo, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 607 days.

(21) Appl. No.: 13/448,791

(22) Filed: Apr. 17, 2012

(65) Prior Publication Data
US 2012/0216812 A1    Aug. 30, 2012

Related U.S. Application Data

(63) Continuation-in-part of application No. PCT/IB2011/050609, filed on Feb. 14, 2011.
(Continued)

(51) Int. Cl.
*A61M 15/08*    (2006.01)
*A61M 16/06*    (2006.01)

(52) U.S. Cl.
CPC .... *A61M 16/0683* (2013.01); *A61M 16/0666* (2013.01)

(58) Field of Classification Search
CPC ........ A62B 18/084; A62B 9/04; A61M 16/06; A61M 2016/0605; A61M 2016/0622;
(Continued)

(56) References Cited

U.S. PATENT DOCUMENTS 3,308,816 A  *  3/1967  Franklin et al. ......... 128/207.11
5,533,506 A     7/1996  Wood
(Continued)

FOREIGN PATENT DOCUMENTS

WO    WO2007075491 A2    7/2007
WO    WO2008007985 A1    1/2008
(Continued)

OTHER PUBLICATIONS

ComfortCurve—Best Practice for Sizing and Fitting, Jun. 16, 2005, Source: http://comfortseries.respironics.eu/pdf/UserGuides/Fitting-GuideComfortCurve.pdf.

*Primary Examiner* — Peter S Vasat
(74) *Attorney, Agent, or Firm* — Michael W. Haas

(57) ABSTRACT

A patient interface assembly includes a support member having a central support portion and a pair of cheek mount supports coupled to the central portion. Each cheek mount support applies a force on or on a side of a user's cheekbone. A seal member is coupled to the support portion and seals against the user. An additional nasal support member is provided that includes a first lateral side member operatively coupled to the central support portion and arranged to be disposed along a first side of a user's nose, and a second lateral side member also operatively coupled the central support portion and arranged to be disposed along a second side of a user's nose. At least a portion of the first lateral side member and the second lateral side member is rigid or semi rigid.

12 Claims, 8 Drawing Sheets

Related U.S. Application Data

(60) Provisional application No. 61/311,586, filed on Mar. 8, 2010.

(58) Field of Classification Search
CPC .. A61M 2016/0627; A61M 2016/0633; A61M 2016/0644; A61M 2016/0655; A61M 2016/0661; A61M 16/0683; A61M 16/0622; A61M 16/0605; A61M 16/0627; A61M 16/0633; A61M 16/0638; A61M 16/0644; A61M 16/0655
USPC .................................................... 128/207.18
See application file for complete search history.

(56) References Cited

U.S. PATENT DOCUMENTS

| | | | |
|---|---|---|---|
| 7,210,481 | B1 | 5/2007 | Lovell |
| 2006/0060200 | A1 | 3/2006 | Ho |
| 2007/0221219 | A1 | 9/2007 | Christy |
| 2008/0190432 | A1 | 8/2008 | Blochlinger |
| 2008/0190436 | A1 | 8/2008 | Jaffe |
| 2008/0245369 | A1* | 10/2008 | Matula et al. ........... 128/205.25 |
| 2009/0044808 | A1 | 2/2009 | Guney |
| 2009/0126739 | A1 | 5/2009 | Ng |
| 2010/0000534 | A1 | 1/2010 | Kooij |

FOREIGN PATENT DOCUMENTS

| | | |
|---|---|---|
| WO | WO2008087468 A1 | 7/2008 |
| WO | WO2010073142 A1 | 7/2010 |

\* cited by examiner

PATIENT INTERFACE ASSEMBLY WITH IMPROVED STABILIZATION

CROSS-REFERENCE TO RELATED APPLICATIONS

This patent application claims the priority benefit under 35 U.S.C. §365(c) as a Continuation-In-Part of International Application No. PCT/IB2011/050609, filed on Feb. 14, 2011, which claims the priority benefit under 35 U.S.C. §119(e) of U.S. Provisional Application No. 61/311,586 filed on Mar. 8, 2010, the contents of each of which are herein incorporated by reference.

BACKGROUND OF THE INVENTION

1. Field of the Invention

The present invention relates to a patient interface assembly for being connected to a patient's respiratory system in order to provide a flow of gas to an airway of the patient and, in particular, to a patient interface assembly that includes cheek mount supports, which use the cheekbone to properly locate and fix the patient interface assembly on the face of the user.

2. Description of the Related Art

There are numerous situations where it is necessary or desirable to deliver a flow of breathing gas non-invasively to the airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient, to the airway of a patient/user. Typical pressure support therapies are provided to treat a medical disorder, such as sleep apnea syndrome, in particular, obstructive sleep apnea (OSA) or congestive heart failure and/or other medical and respiratory disorders, such as Cheynes-Stokes respiration, congestive heart failure, and stroke.

Non-invasive ventilation and pressure support therapies involve the placement of a patient interface assembly, which is typically a nasal or nasal/oral mask, on the face of a patient to interface the ventilator or pressure support system with the airway of the patient so that a flow of breathing gas can be delivered from the pressure/flow generating patient interface assembly to the airway of the patient. It is known to maintain such masks on the face of a patient by a headgear having upper and lower straps, each having opposite ends threaded through connecting elements provided on the opposite sides and top of a mask.

Because such masks are typically worn for an extended period of time, a variety of concerns must be taken into consideration. For example, in providing a pressure support therapy to treat OSA, the patient normally wears the patient interface patient interface assembly all night long while he or she sleeps. Patient interface development has generally involved balancing of two competing goals: a) secure attachment to and seal with the user's face to create an airtight seal in order to facilitate the required positive airway pressure, and b) comfort to the user in order to maximize patient compliance, i.e., usage of the medical therapy. An airtight seal can be achieved by tightening the mask down firmly against the patient's face. However, this solution often results in discomfort to the user due to relatively high strapping forces needed to ensure a secure seal against the patient and less than satisfactory patient compliance. Alternatively, the mask may be fit loosely on the patient's face to enhance comfort. However, the effectiveness of the mask may be compromised if it is too loose.

PCT application no. PCT/IB2011/050609 (PCT publication no. WO 2011/110961)("the '961 application"), the contents of which are incorporated herein by reference, describes a patient interface assembly is described that includes a support member comprising a central support portion and a pair of cheek mount supports coupled to the central portion. Each cheek mount support is configured to apply a force a side a user's cheekbone while applying substantially no force over an apex of such a user's cheekbone responsive to the patient interface assembly being worn by a user. A seal member is coupled to the support portion. The seal member is adapted to seal against a surface of a user to communicate a flow of gas with an airway of such a user. A conduit coupling member is coupled to the seal member. The seal member comprises two conical nasal prongs, adapted for being inserted in the nasal passages of the patient.

The stability and fixation of the seal member and nasal prongs is obtained by the central support which is connected with cheek mount supports which are in contact with the face of the patient in the area around the cheekbone.

It is believed that the stability of the seal member and, if present, nasal prongs can further be improved. There exists a need for such a further improvement in industry.

SUMMARY OF THE INVENTION

Accordingly, it is an object of the present invention to provide a patient interface assembly comprising cheek mount supports that overcomes the shortcomings of conventional patient interface assembly. This object is achieved according to embodiments of the present invention by providing a patient interface assembly that includes an additional nasal support member that includes a first lateral side member having a first end operatively coupled to a second side of the central support portion and arranged to be disposed along a first side of a user's nose. The additional nasal support member also includes a second lateral side member having a first end operatively coupled to a second side of the central support portion and arranged to be disposed along a second side of a user's nose. At least a portion of the first lateral side member and the second lateral side member is rigid or semi rigid.

Particular aspects of the invention are set out in the accompanying independent and dependent claims. Features from the dependent claims may be combined with features of the independent claims and with features of other dependent claims as appropriate and not merely as explicitly set out in the claims.

According to a first aspect of the present invention, a patient interface assembly is disclosed comprising a support member comprising a central support portion and a pair of cheek mount supports coupled to the central portion. Each cheek mount support is configured to apply a force on or on a side of a user's cheekbone. A seal member is operatively coupled to the support portion and being adapted to seal against a surface of a user to communicate a flow of gas with an airway of such a user. An additional nasal support member is provided that comprises a first lateral side member having a first end operatively coupled to a second side of the central support portion and arranged to be disposed along a first side of a user's nose, and a second lateral side member having a first end operatively coupled to a second side of the central support portion and arranged to be disposed along a second side of a user's nose. At least a portion of the first lateral side member and the second lateral side member is rigid or semi rigid.

The presence of the additional nasal support member provides an increased stability of the patient interface assembly when being used by the user. The semi rigid or rigid side members can for instance allow a transfer of forces towards the nasal area without substantially deforming.

According to exemplary embodiments of the present invention, the seal member further comprises a pair of nasal prongs for being inserted in the nasal passages of the patient when communicating a flow of gas to an airway of the patient.

During wear of the patient interface assembly by a user, different forces may act on the device. According to the prior art, a relatively big component of those forces is or can be transferred to the nose, even more when nasal prongs are present and inserted in the nasal passages of the user. Another component is or can be transferred to the lower nose area, comprising the upper lip, the area between the upper lip and the nose and the bottom outer surface/skin of the nose, especially by the seal member which may be in contact with at least part of the lower nose area. It is an advantage of embodiments of the present invention that at least one of these components can be limited or avoided. This is achieved by redirecting or at least partially compensating the possibly induced forces during wear towards the nasal area of the user. It will be appreciated that the nasal area is an area that is suitable for such additional nasal support member to support or work on, as at least part of this area is typically used when wearing glasses.

It can be noted that different cheek mount supports exist to apply a force on or a side a user's cheekbone for supporting the patient interface assembly, more specifically for positioning it on the user's face. Some of these cheek mount supports may pass over the apex or may apply such a force on the apex. Such cheek mount supports can be used according to embodiments of the present invention.

Typically the patient interface assembly comprises also a conduit coupling member operatively coupled to the seal member. The conduit coupling member can be coupled to a first end of a conduit, which is arranged for providing a gas to the user. The conduit can be coupled at a second end to a pressure support system.

The seal member can be seen as an adapter for guiding a gas between the conduit coupling member and the patient, for instance but not only by means of nasal prongs.

Typically, the patient interface also comprises a headgear assembly operatively coupled, coupled, or directly coupled to the cheek mount support for fastening and positioning the patient interface assembly to the user.

According to various embodiments of the present invention, the additional nasal support member is adapted for applying a stabilizing force on a lacrimal bone and/or maxilla of the user responsive to the patient interface assembly being worn by the user. The stabilizing force is acting on the upper part, for instance the upper half of the maxilla. In another view, the additional nasal support member can be further configured, or arranged and adapted, to generate a stabilizing force acting between the lacrimal bone and/or maxilla of the user and the patient interface assembly, responsive to the patient interface assembly being worn by the user.

The configuration of the additional nasal support member and the lacrimal bone or maxilla of the user can be such that only pushing forces can be applied on the maxilla or lacrimal bone by the additional nasal support member.

Therefore, no adhesive coupling, or more generally, no fixed coupling or attachment has to be applied in between the additional nasal support member and the lacrimal bone or maxilla. Direct or indirect adhesive coupling between the additional nasal support member and the maxilla or lacrimal bone would otherwise result in pulling forces being exerted on the lacrimal bone or maxilla (or lacrimal bone area or maxilla area). Moreover, the use of adhesives may also reduce comfort or cause allergic reactions of the user/patient.

According to other embodiments of the present invention, the additional nasal support member further comprises a connection member adapted for coupling a second end of the first lateral side member with a second end of the second lateral side member. Thereby an arch-shaped or U-shaped type structure can be formed.

According to further embodiments of the present invention, the additional nasal support member is adapted and/or arranged for applying a stabilizing force on the nasal bone of the user responsive to the patient interface assembly being worn by the user. In another view, the additional nasal support member can be further configured, or arranged and adapted, to generate a stabilizing force acting between the nasal bone of the user and the patient interface assembly, responsive to the patient interface assembly being worn by the user.

The configuration of the additional nasal support member and the nasal bone of the user can be such that only pushing forces can be applied on the nasal bone by the additional nasal support member. Therefore, no adhesive coupling, or more generally, no fixed coupling or attachment has to be applied in between the additional nasal support member and the nasal bone. Direct or indirect adhesive coupling between the additional nasal support member and the nasal bone would otherwise result in pulling forces being exerted on the nasal bone (or nasal bone area). Moreover, the use of adhesives may also reduce comfort or cause allergic reactions of the user/patient.

According to still other embodiments of the present invention, the additional nasal support member is configured for applying a stabilizing force which at least partially limits a force component exerted on a lower nose area of the patient by the sealing member and, if present, by the nasal prongs, responsive to the patient interface assembly being worn by a user, the stabilizing force acting between the patient interface assembly and a nasal area, for instance an upper nasal area, of the user. The nasal area can be defined by or can comprise the nasal bone (comprising the bridge of the nasal bone and the sidewalls of the nasal bone), the maxilla (upper part or half, and lower part or half) and the lacrimal bone. The upper nasal area can be defined by or can comprise the nasal bone, lacrimal bone and the upper half of the maxilla. The lower nasal area can comprise the lower half of the maxilla and the lower part of the nose as well as the skin area between the nose and the upper lip of the patient, the bottom skin of the noes, and the upper lip.

According to further embodiments of the present invention, the additional nasal support member is directly coupled with the support member and further comprises at least one discrete contact point or contact area (e.g. on the nasal none, e.g. on the nose bridge), but for instance also two (e.g. two symmetrically positioned on the user's face (e.g. on left and right upper maxilla)) or three discrete contact points or contact areas (both, one on the nasal bone and two symmetrically positioned on the user's face), with the user's nasal area when the patient interface assembly is worn by the user, and wherein the additional nasal support member is adapted for not coming in contact with a user's face except for the at least one (or two, or three) discrete contact points responsive to the patient interface assembly being worn by the user.

This brings the advantage that, at design time for the patient interface assembly, more generic assumptions can be made about typical users. This can result in more generically applicable patient interface assemblies, i.e. patient interface assemblies suitable for a wider set of users or user types. Moreover simulations of force distributions can more easily be made. During wear of the patient interface assembly, it is also experienced as being more comfortable. Also, the contact region can be provided with, or can only be provided with, or can comprise, certain comfort-improving materials or features.

According to exemplary embodiments of the present invention, the cheek mount supports comprise a first member that is adapted to pass below the apex of the cheekbone when the patient interface is being worn by such a user, and such that no substantial translation of the cheek support member towards the eye, in a first direction defined by a straight line connecting the cheek bone apex and the eye of the user, is possible responsive to the patient interface assembly being worn by a user; and the additional nasal support member is adapted and arranged such that it limits the force exerted on the seal member and possibly nasal prongs, by limiting a translational movement of the cheek mount support member in a direction substantially perpendicular to the first direction.

According to still further embodiments of the present invention, the cheek mount supports comprise a first member that is adapted to pass below the apex of the cheekbone when the patient interface is being worn by such a user, and such that no substantial translation of the cheek mount support member towards the eye, in a first direction defined by a straight line connecting the cheek bone apex and the eye of the user, is possible responsive to the patient interface assembly being worn by a user. The additional nasal support member is adapted and arranged such that it limits the force exerted on the seal member, and possibly on the nasal prongs, by further limiting a rotational movement of the cheek mount support member (along e.g. an axis defined by the cheekbone apex) responsive to the patient interface being worn by a user.

According to other embodiments of the present invention, the cheek mount support member further comprises a second member that is adapted to pass between an apex of a cheekbone and an eye of a user when the patient interface is being worn by such a user; and wherein the first member and the second member are fixedly coupled to each other such that they define an opening, the opening adapted for receiving the apex of the user's cheekbone, and such that no substantial translation of the cheek mount support member away from the eye, in the first direction, is possible responsive to the patient interface assembly being worn by a user.

According to yet other embodiments of the present invention, the first member and the second member are joined at each end to define a loop-shaped structure, and wherein the looped-shaped structure is sized and configured to substantially encircle an apex of a cheekbone of a user responsive to the patient interface assembly being worn by such a user.

According to further embodiments of the present invention, each cheek mount support fully encircles an apex of an associated cheekbone. This may further improve stability of the patient interface assembly on the user's face.

According to still other embodiments of the present invention, the support member and the additional support member are unitary. The support member and the additional nasal support member are substantially rigid, as this provides a very good stability of the patient interface assembly on the face of the patient. But the support member and the additional nasal support member can be both semi-rigid. The support member can be semi-rigid and the additional nasal support member can be rigid. Or the support member can be rigid and the additional nasal support member can be semi-rigid. In an exemplary embodiment, a soft interface as for instance a cushion or soft contact pad can be present or provided in the contact area between the additional nasal support member and the user's face, to improve comfort. For instance, a silicone or soft textile or foam material portion can be comprised in the contact area for interfacing with the patient's skin.

According to other embodiments of the present invention, the support member and the additional nasal support member comprise metal, plastic, or a combination thereof. Other materials as for instance wood (e.g. bamboo) or composites of fibers/cloth/glass/carbon and glue/epoxy etc. which are known to the skilled person can be used.

According to even further embodiments of the present invention, the seal member is rotatably coupled to the support member. This can allow a more efficient installation of the patient interface assembly on the user. This can also increase comfort for the user, as this may constitute a limited movement "buffer" for external forces being induced on the seal member and possibly nasal prongs, thus on the nose and/or lower nose area. Such forces may be at least partially compensated or redirected for by a rotating movement of the seal member. Also, having a rotatably mounted seal member can make the patient interface more generic in use.

According to other embodiments of the present invention, the cheek mount supports comprise a first end portion positioned towards a central part of the user's face and a second end portion positioned further away from the central part, when the patient interface assembly is worn by the user, further comprising a stabilization element which couples the additional nasal support member with the second end portion of the cheek mount support and which is adapted for maintaining a contact between the additional nasal support member and the nasal area responsive to the patient interface assembly being worn by the user.

It is an advantage of having the stabilization element that stability of the patient interface assembly can further be improved. According to exemplary embodiments, the stabilization element is at least partially, or fully, elastic. It can for instance be an elastic strap. An elastic stabilization member can be arranged and adapted such that it preloads a force pulling the nasal support member towards the user's face during use.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EMBODIMENTS

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body.

Figure 1:
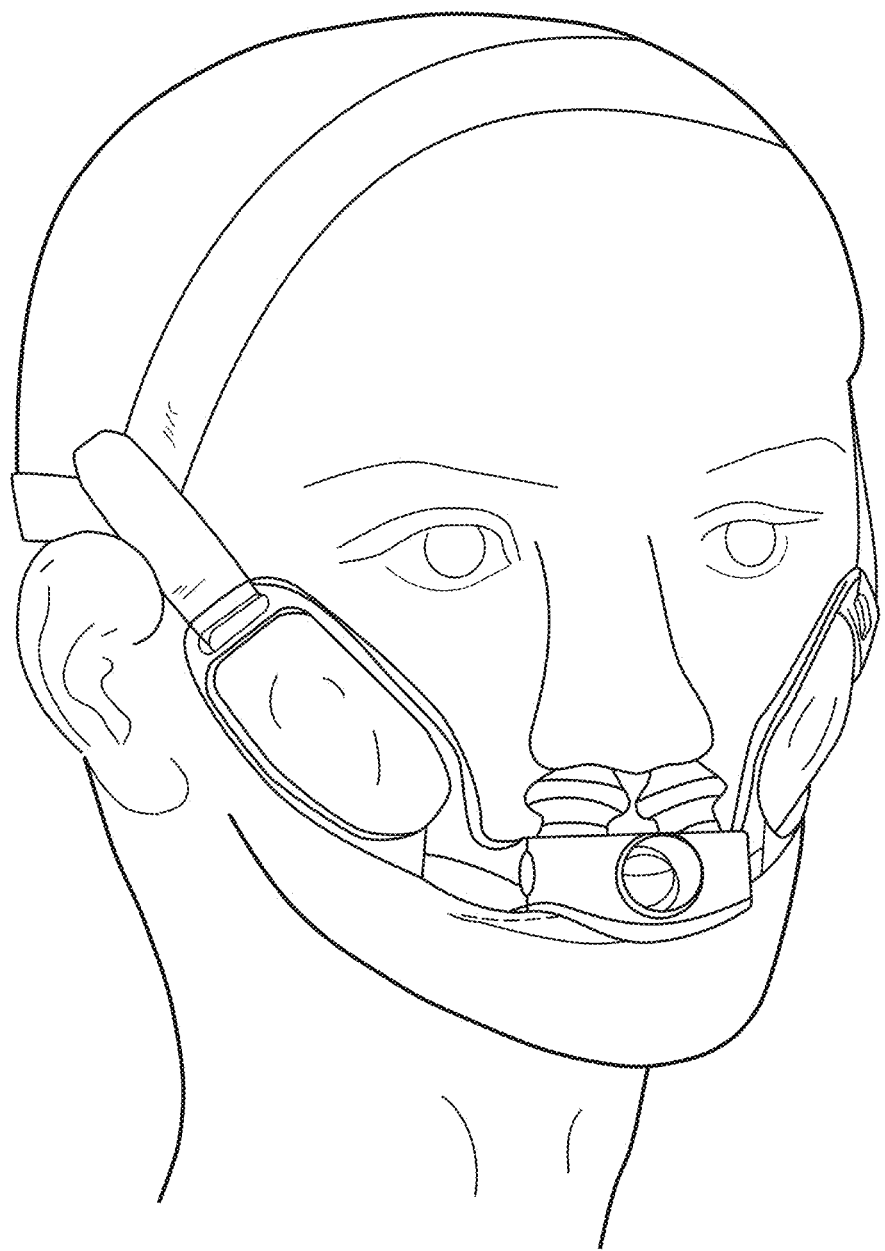
FIG. 1 is a perspective view of a patient interface assembly disclosed in the '961 application.

FIG. 1 illustrates the patient interface assembly according to the '961 application. A patient interface assembly is described that includes a support member comprising a central support portion and a pair of cheek mount supports coupled to the central portion. Each cheek mount support is configured to apply a force a side a user's cheekbone while applying substantially no force over an apex of such a user's cheekbone responsive to the patient interface assembly being worn by a user. A seal member is coupled to the support portion. The seal member is adapted to seal against a surface of a user to communicate a flow of gas with an airway of such a user. A conduit coupling member is coupled to the seal member.

The seal member comprises two conical nasal prongs, adapted for being inserted in the nasal passages of the patient. The stability and fixation of the nasal prongs is obtained by the central support which is connected with cheek mount supports which are in contact with the face of the patient in the area around the cheekbone. Forces exerted directly or indirectly on the nasal prongs and/or seal member, responsive to the patient interface being worn by a user, can though still be very uncomfortable for the user and may moreover break the airtight seal which is preferably present between the outer surface of the nasal prongs and the internal surface of the nasal passages. The sidewall of the nose and/or lower nose area has to compensate forces resulting from translational or rotational movement of the nasal prongs. The nasal prongs can also be pushed further into the nose due to such forces, above an uncomfortable level.

Figure 2A:
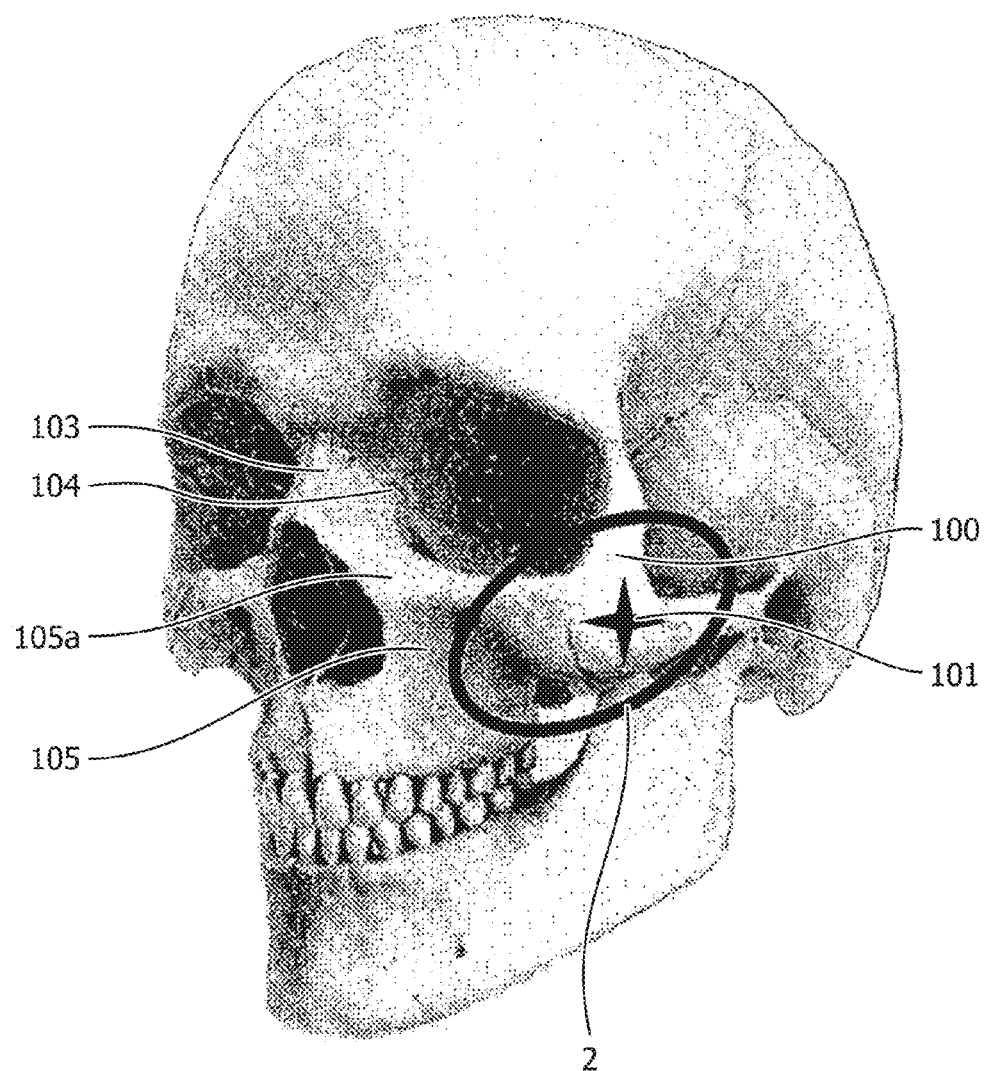
FIG. 2A is a perspective view of a human skull illustrating the cheekbones and other shape characteristics of a human skull, with support portions according the '961 application.

In FIG. 2A, a human skull is depicted. The skull comprises a cheek bone 100 (also zygomatic bone) and the position of a cheek mount support 2 of the patient interface assembly 1 with respect to the skull is illustrated, as it is positioned in the '961 application. The cheek bone comprises an apex 101, being a peak portion which is a portion protruding the furthest from the face (approximately indicated throughout the figures with a "star"). The cheek mount support is positioned with respect to the cheekbone by applying a force a side the cheekbone.

Figure 2B:
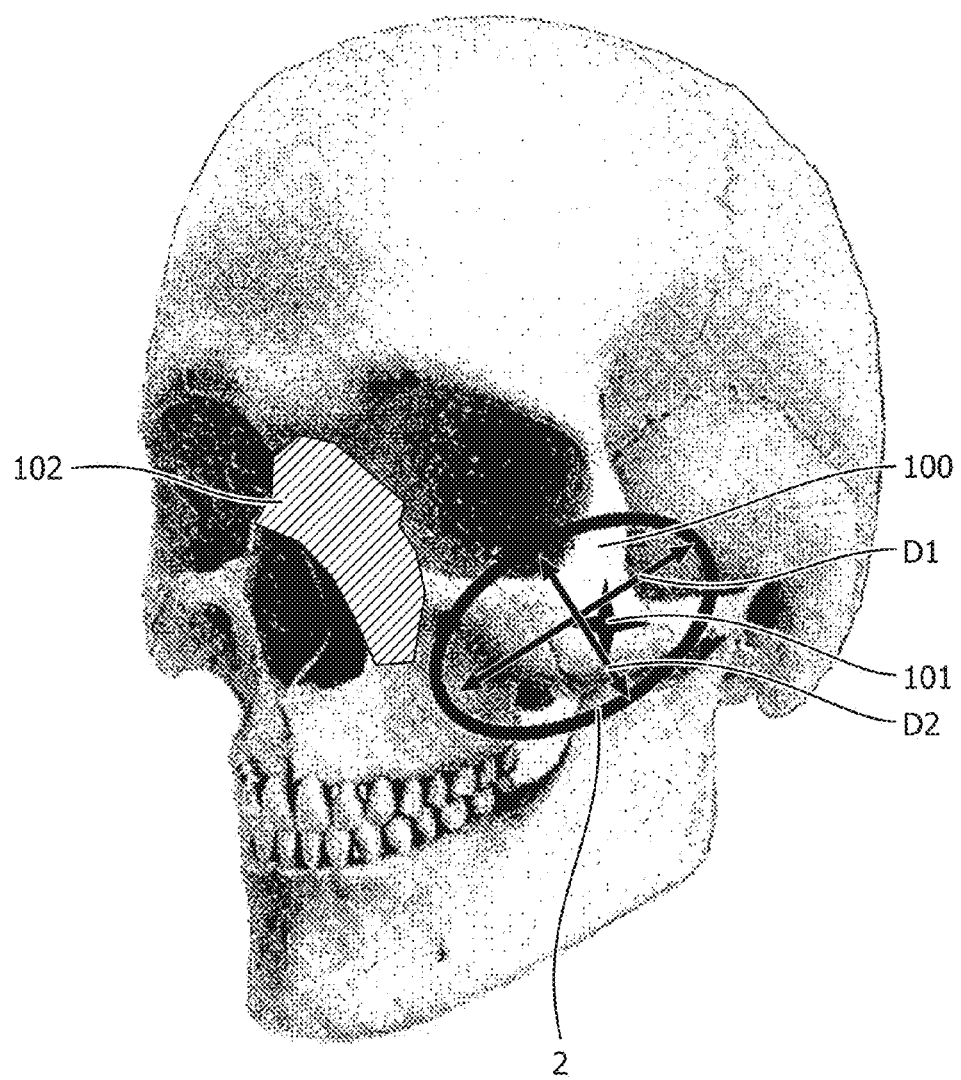
FIG. 2B is a perspective view of a human skull illustrating the cheekbones and other shape characteristics of a human skull, with extra support portions according to aspects of the '961 application.

In FIG. 2B, the same human skull is depicted. Area 102 describes the area of the user whereon an additional nasal support member of a patient interface assembly 1 is arranged, according to embodiments of the present invention, in order to apply a stabilizing force responsive to the patient interface assembly being worn by the user. This area covers the nasal bone 103, the lacrimal bone 104 and the maxilla bone 105, such as the upper part or half of the maxilla bone 105a. Typically, the patient comprises a skin covering the skull, but as the forces are eventually applied or carried by the rigid bone structure, i.e. the skull, portions of the skull have been referred to for the purpose of the present description. Note that alternatively the cheek mount support may also pass over the apex, and can be in contact with the (skin covering the) apex.

Figure 3A:
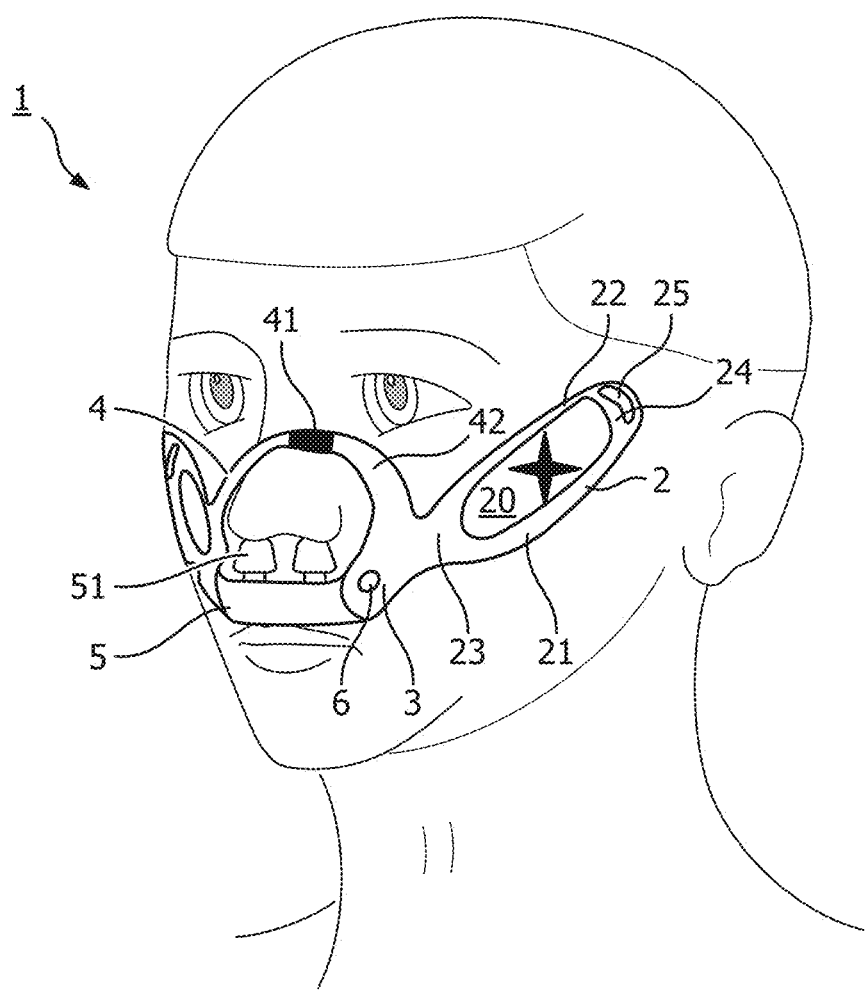
FIG. 3A is a perspective view of a first embodiment according to aspects of the present invention.

FIG. 3A illustrates a patient interface assembly 1 according to a first embodiment, when positioned on the face of a user or patient. The patient interface device 1 comprises two cheek mount supports 2 (one on the left and one on the right side of the face), which are coupled to each other via a central portion 3, which in this case is partially formed by a seal member 5 performing also the function of the central portion. The seal member 5 is coupled, operatively coupled, in this embodiment also fixedly coupled, to the support portion (2,3), for example near the first end portion 23 (forming a "limited" central support 3) of the cheek mount support 2. The seal member 5 is adapted to seal against a surface of a user to communicate a flow of gas with an airway of such a user. The seal member 5 can therefor comprise a pair of nasal prongs 51 which are adapted for being inserted into the patient's nasal passages and to hereby make a substantially or completely airtight seal with the internal surface of the nasal passages of the patient. The seal member does perform, at least partially, the function of the central portion 3.

Further, typically a conduit coupling member 7 (not depicted, but similar as in FIG. 6) is coupled to the seal member 5. The conduit coupling member is connected with a conduit or circuit (not depicted), which connects the patient interface assembly with a pressure support system (not depicted). The seal member 5 comprises internal channels which distribute the inflow or outflow of gas to appropriate locations. For instance, internal channels can be provided which distribute the inflow of gas towards the nasal prongs 51.

Note that alternatively the central portion 3 can be independent from the seal portion 5 or can comprise more than only the seal portion 5, as will be clear from further embodiments described below.

Each cheek mount support 2 includes a first member 21 and a second member 22, which, in the illustrated embodiment, are coupled at first end portion 23 and second end portion 24 of the cheek support member. In this manner, each cheek mount support has a loop-shaped structure having an opening 20 defined between the first and second members. Each cheek support member 2, and, in particular, the first and second members and their interconnections that define the loop-shaped structure, are sized and configured such that when patient interface assembly 2 is worn by the user, the loop-shaped member is configured to be disposed over opposing sides a user's cheekbone while not being disposed over an apex 101 of such a user's cheekbone.

Stated another way, zygomatic bone (also called cheekbone) has a peak portion 101, i.e., a portion that protrudes the furthest from the face. In an exemplary embodiment, no part of cheek mount support applies a force against peak portion 101 of the cheekbone. Instead, the peak portion of the cheek bone protrudes through opening 20 of cheek support mount 2 so that first member 21 and second member 22 rest on either side of the cheekbone. In the illustrated embodiment, cheek support member 2 fully encircles, but does not pass over the apex of, a user's cheek area. Each cheek mount support is configured to apply a force a side a user's cheekbone while applying substantially no force over an apex of such a user's cheekbone when the patient interface assembly being worn by a user.

The spacing between first member 21 and second member 22, i.e., the width of opening 20, as indicated by dimension D2 in FIG. 2B, can for instance range from 1 to 8 cm, or from 2 cm to 6 cm. The spacing between first end portion 23 and the second end portion 24, i.e., the length of opening 20, as indicated by dimension D1 in FIG. 2B can for instance range from 1 cm to 12 cm or from 2 cm to 10 cm. This range of dimensions ensures that the components of cheek mount support 2 remain over the sides of the cheekbone but are not disposed over the apex of the cheekbone. As a result, the cheekbone and overlying tissue becomes a support structure for holding the patient interface assembly in place on the face. Using opening 20 to "capture" or "anchor" to the cheekbone also provides for easy alignment of support member on the user's face and enhances the stability of the support member of the face, and thereby decreasing leaks and patient discomfort.

Although probably less comfortable in wear and/or intrinsically less stable, alternatively, other state of the art cheek mount supports can be used instead. This can be, for instance, cheek mount supports that do pass over the apex of the user, such as, for instance, the cheek mount supports as described above which additionally pass over the apex of the user, thereby possibly exerting a pressure on the cheekbone of the user. Or cheek mount supports which are positioned with respect to the cheek bone by exerting a pressure on the cheek bone area, and not around the cheek bone area.

Figure 6:
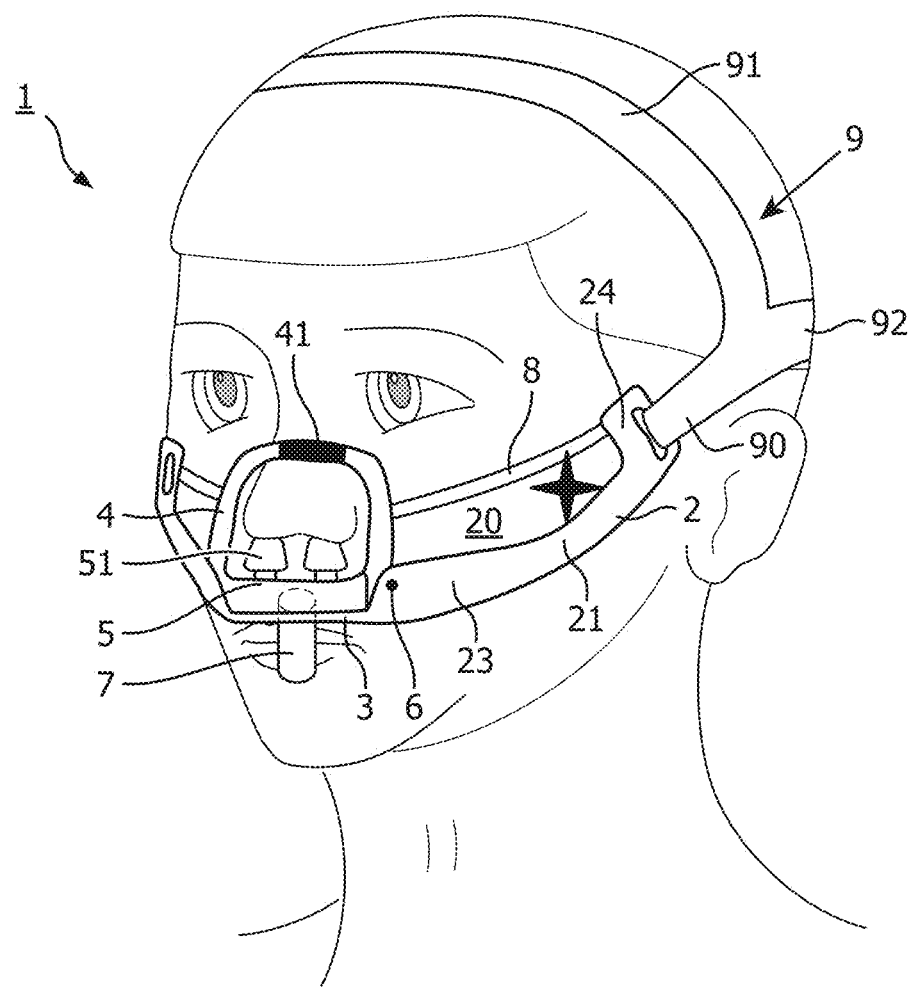
FIG. 6 is a perspective view of a fifth embodiment according to aspects of the present invention.

The cheek mount supports 2 comprise a coupling member 25 (e.g. an opening or similar means) near their second end portion 24 for coupling with a head strap or head gear 9 (not depicted, but for instance as in FIG. 6). Such a head gear 9 can comprise on both sides of the patient's head, a first strap 90 which is connected to the cheek mount support 2 by means of the coupling member 25 on one end and which bifurcates into two further straps 91 and 92, the respective further straps of both cheek support members being connected to each other. The strap formed by the first straps 91 may for instance pass over the top of the head of the user, while the strap formed by the second straps 92 may for instance pass over the back of the head.

The cheek mount supports as described above, in the main and alternative embodiments, further cooperate with an additional nasal support member 4, thereby avoiding or reducing the movement of the nasal prongs during use of the patient interface assembly 1. Such a movement, and resulting forces on the internal of the nose, may be experienced as still very uncomfortable to the user and as such a movement may break or change the properties of the airtight seal between the nasal prongs and the internal surface of the nasal passages of the patient. The additional nasal support member 4 is being configured to apply a stabilizing force on the user's face in a nasal area responsive to the patient interface assembly being worn by the user, and thereby limits, reduces or avoid the presence of additional forces which would otherwise (in the case of cheek mount support without such an additional nasal support member) be acting on the user's nose and/or lower nose area, especially on the nasal passages of the user, during use of the patient interface assembly. The additional nasal support member can for instance be or comprise an element 42 of the "arch"-type or can be "arch"-shaped or "U"-shaped. The "arch"-type element is here fixedly connected to the first end portions of the respective cheek mount supports 2.

The additional nasal support member 4 comprises a limited contact area with the nose area of the patient when in use. The total contact area, corresponding for instance to one, two or three distinct contact points or areas, may for instance be smaller than 5 cm2 or smaller than 4 cm2 or smaller than 3 cm2 or smaller than 2 cm2 or smaller than 1 cm2. This may increase comfort, but also allows an efficient development of generic patient interface assemblies, as force and pressure points can be identified. In case of an extended contact surface between the additional nasal support member and the skin of the nasal area of the patient, comfort is reduced and force and pressure distribution can more difficultly or not be estimated. The additional nasal support member 4 thus comprises one or more limited contact portions 41.

Figure 3B:
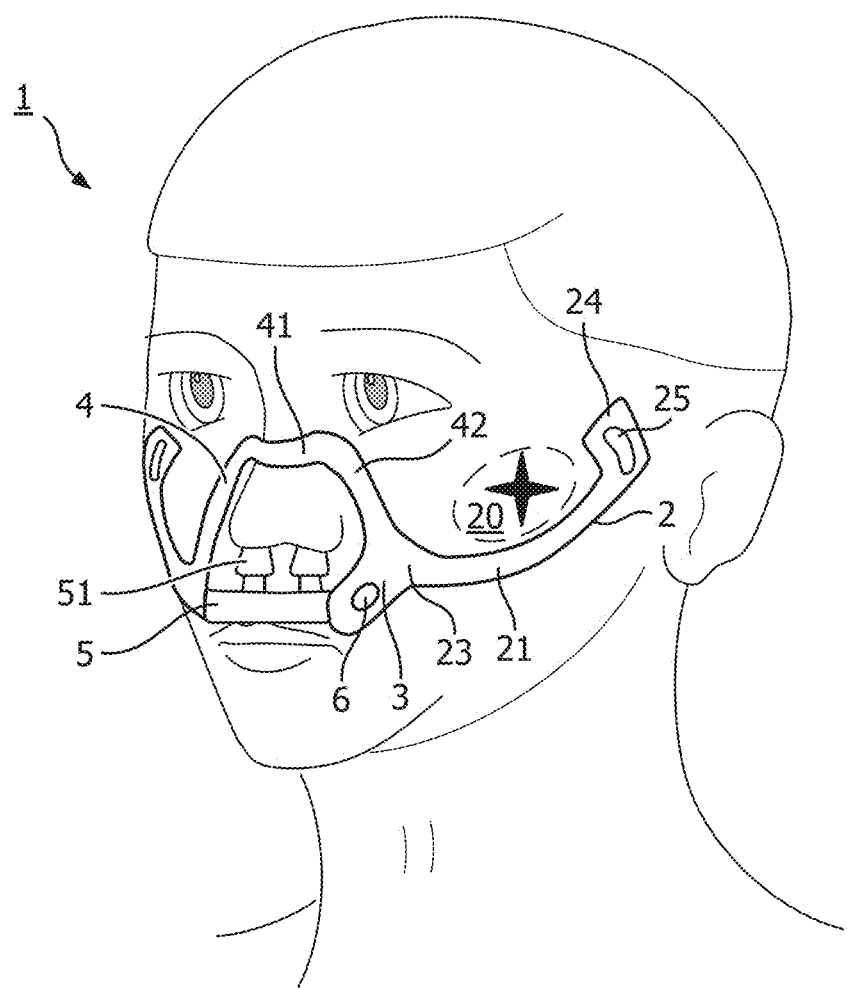
FIG. 3B is a perspective view of a second embodiment according to aspects of the present invention.

FIG. 3B illustrates a patient interface assembly 1 according to a second embodiment, when positioned on the face of a user. The device is similar to the device of the first embodiment, but comprises a different cheek mount support. The cheek mount support only comprises a first member 21, and no second member 22. The first member is adapted to pass below the apex of the cheekbone when the patient interface is being worn by the user, and such that no substantial translation of the cheek support member towards the eye, in a first direction defined by a straight line connecting the cheek bone apex and the eye of the user, is possible responsive to the patient interface assembly being worn by a user.

Figure 4:
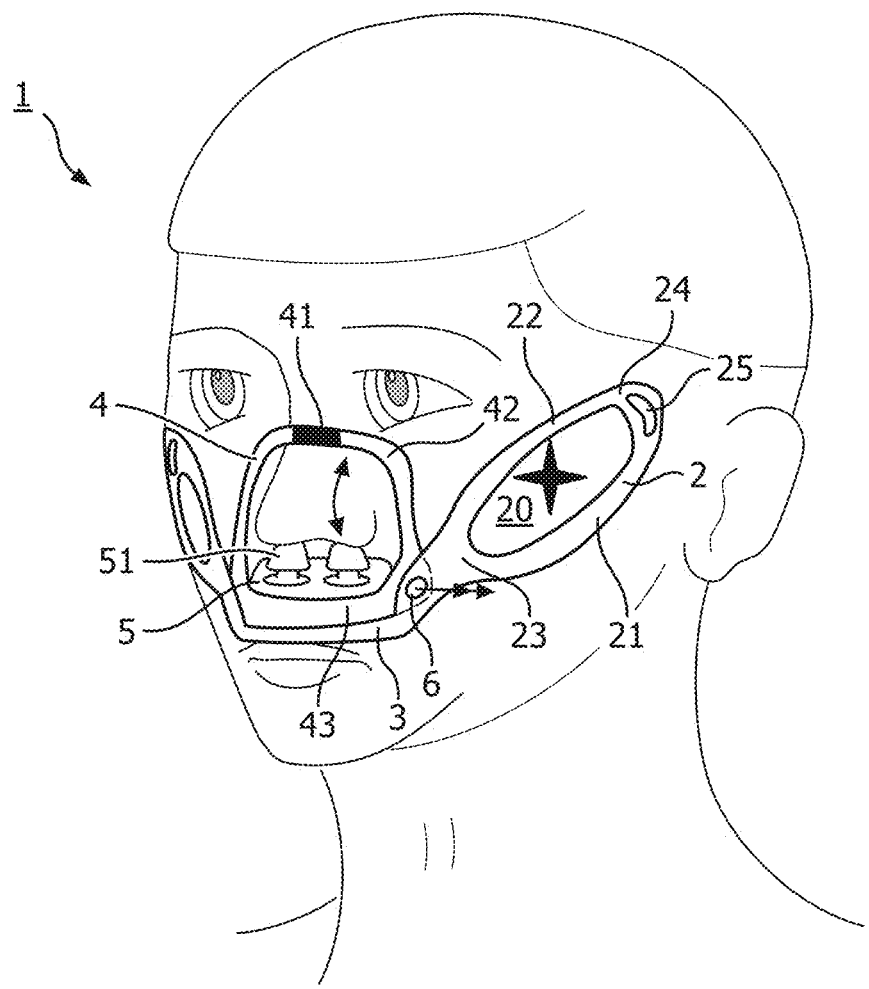
FIG. 4 is a perspective view of a third embodiment according to aspects of the present invention.

FIG. 4 illustrates a patient interface assembly 1 according to a third embodiment, when positioned on the face of a user or patient. The cheek mount supports 2 are identical to those described for the first embodiment. A central portion 3 is now present, independent from the seal member 5, which connects the two cheek mount supports 4. The head strap or head gear 9 is not depicted, but is similar to the first embodiment.

According to the third embodiment, the additional nasal support member 4 comprises again an arch portion 42, having a limited contact portion 41, and is adapted for providing a limited contact surface with the patient's nose (in this case the nasal bone) by means of the contact portion 41, when the patient interface assembly is being worn by the user. The arch portion 42 is though not fixedly coupled, but pivotably or rotatably coupled with the support member 2, 3. A pair of pivots 6 is provided between the arch member 42 and the support member 2, 3, near the first ends of the respective cheek mount supports 2. The rotational movement of the additional nasal support member can be towards the nose or away from the nose. The rotation away from the nose can be limited by a counter momentum, for instance caused by e.g. elastic strap (FIG. 6) or spring loaded pivot element 6 or blocking portion 43. The rotation towards the nose can be damped by a soft interface of foam/gel at contact portion 41. The angle of the prongs 5 can further possibly be adjusted by an additional (not depicted) adjustment element which can be located at the contact portion 41 and/or at the blocking portion 43. In an exemplary embodiment, it is present in at least the region between the skin touch points and the rotatable frame 42, 43.

Moreover, the additional nasal support member is also fixedly coupled with the seal means 5, such that the additional nasal support member and seal means can rotate along an axis defined by the two pivots 6. Further, a blocking portion 43 can be comprised in the additional nasal support member 4, which is adapted for limiting the available rotation angle of the arch portion 42 and seal means 5. The coupling between the additional nasal support member 4 and the seal means 5 can be performed by means of such a blocking portion 43. The blocking portion may cooperate during use with (part of) the central portion 3, wherein the (part of the) central portion 3 blocks a further rotation of the additional nasal support member when both elements get into physical contact upon initial rotation of the additional nasal support means.

Figure 5:
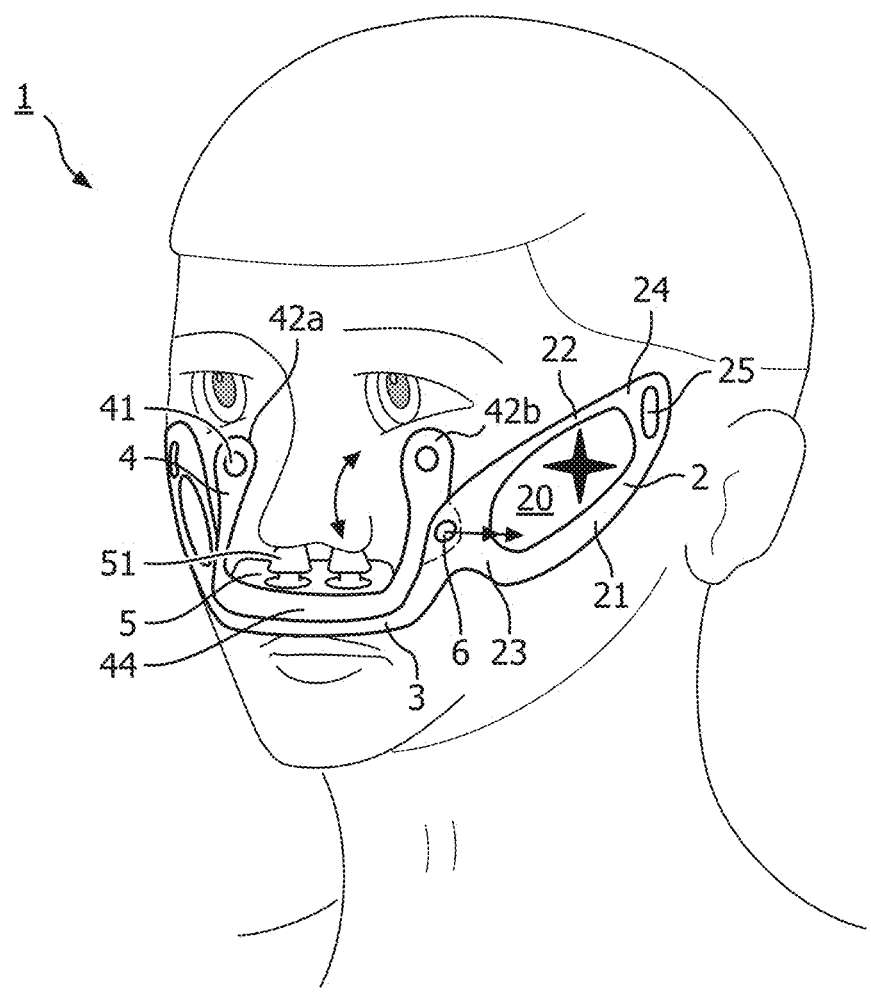
FIG. 5 is a perspective view of a fourth embodiment according to aspects of the present invention.

FIG. 5 illustrates a patient interface assembly 1 according to a fourth embodiment, when positioned on the face of a user or patient. This device is very similar to the device depicted in FIG. 4 and described therewith. The additional nasal support member is also rotatably coupled to the support member (2,3) as described for the third embodiment, and carries the seal means 5, for instance it can also be fixedly coupled with the seal means 5. The difference with the device according to the third embodiment of the present invention lies in the arrangement and shape of the additional nasal support member 4. Instead of an arch-portion 42, the device according to the fourth embodiment of the present invention comprises two support protrusions 42*a*, 42*b*— which are pivotable around the pivots 6. The two support protrusions 42*a*, 42*b* are adapted for being brought in contact with the user's nasal area (for instance on the nasal bone, side of the nasal bone or upper part of the maxilla), each on a different side of the nose, by means of limited contact portions 41. The support protrusions 42*a* and 42*b* are further connected to each other by means of a connecting portion 44. This connecting portion 44 may also play the role of blocking portion 43 as described for the third embodiment. The connecting portion 44 is for instance fixedly coupled or connected to the seal means 5, or the connecting portion 44 may comprise the seal means. The connecting portion can be constituted by the seal means 5.

It is believed that rotation of the seal means (and additional nasal support member, to which is may be fixedly coupled) around the pivots 6, although not being necessary, may improve comfort in installation and wear of the patient interface assembly, contrary to translations along and rotations around the cheekbone which are possible if no additional nasal support means would be present.

FIG. 6 illustrates a patient interface assembly 1 according to a fifth embodiment, when positioned on the face of a user or patient. The patient interface assembly 1 according to the fifth embodiment comprises a rotatably mounted additional nasal support member 4, pivotably along axis defined by pivots 6, as described for the third embodiment, but possibly also as described for the fourth embodiment (the latter not depicted though).

The patient interface assembly 1 according to the fifth embodiment comprises a cheek mount support 2 comprising only a first member 21 that is adapted to pass below the apex of the cheekbone responsive to the patient interface assembly being worn by the patient, and such that no substantial translation of the cheek support member towards the eye, in a first direction defined by a straight line connecting the cheek bone apex and the eye of the user, is possible responsive to the patient interface assembly being worn by a user. No second member 22, as described for the other embodiments, is present, but an connecting member (e.g. an elastic strap) 8 is provided in the area in between the apex of the cheekbone and the eye of the patient, extending from the second end 24 of the cheek mount support 2, to which it is connected on one end, to the (e.g., upper part) of the "arch"-type member 42 or to the respective support protrusions 42*a*/*b*, to which it is connected on another end.

The connecting member 8 is elastic and is adapted and arranged for preventing the additional nasal support member 4 to be lifted from the nose area when the client interface device is in use. Moreover, the connecting member 8 may also perform a function similar to the function of the second member 22 of the cheek mount support 4 described for the other embodiments: it may for instance limit the movement of the cheek mount support member toward the eye of the patient. In FIG. 6, an example of a head strap or head gear 9 is depicted, as well as a conduit coupling member 7 connected to the seal means 5.

The cheek support member 2, as well as the additional nasal support member, can be made from or can comprise a flexible, semi-rigid, or rigid material serving as a frame. For instance, materials used can be soft and comfortable, but have enough stiffness in order to allow appropriate force distribution without deforming substantially. e.g. silicone or a silicone overmolded or gel filled frame.

Some or each cheek support member, and/or the contact portion(s) 41, can include a pad (not depicted) provided between the frame and the surface of the user, for increased comfort during wear and/or for better adhesion to the skin. This pad can be formed from any suitable material such as for instance a silicone, foam, plastic, rubber, gel or a combination thereof.

he patient interface assemblies according to any of the embodiments of the present invention can be connected to a pressure support system via a patient circuit, which communicates a gas from the pressure support system to the patient interface assembly. A patient circuit or conduit can be or comprise any device, such as a flexible tubing, that carries the flow of gas from the pressure/flow generator in the pressure support system to the patient interface assembly.

The pressure support system can be any conventional ventilation or pressure support system. Examples of such pressure support systems include, but are not limited to: a ventilator, continuous positive airway pressure (CPAP) device, or a variable pressure device, e.g. an auto-titrating device, proportional assist ventilation (PAV®) device, proportional positive airway pressure (PPAPO) device, C-Flex device, Bi-Flex device, or a BiPAP® device manufactured and distributed by Philips Respironics, Inc. of Pittsburgh, Pa., in which the pressure provided to the patient varies with the patient's respiratory cycle so that a higher pressure is delivered during inspiration than during expiration, or other pressure support device. Other devices that communicate a flow of gas with an airway of a patient suitable for use in with the present invention include devices that apply a high and low or positive and negative pressure to the airway for purposes of secretion clearance or loosening.

The patient circuit can have any suitable configuration. For example, the patient circuit can be a single-limb tubing between the pressure support system and the patient interface assembly. Alternatively, the patient circuit can be a dual-limb tubing system; having an inspiratory limb for carrying a flow of gas to the user and a expiratory limb for carrying a flow of gas from the user. Typically, a Y-connector is provided near the patient that connects the inspiratory and expiratory limbs to the patient interface assembly.

It is to be further understood that various components may be provided in or coupled to pressure support system, patient circuit, patient interface assembly, or any combination thereof. For example, a bacteria filter, pressure control valve, flow control valve, pressure/flow/temperature/humidity sensor(s), meter, pressure filter, humidifier, and/or heater can be provided in or attached to the patient circuit.

The present invention has been described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Other arrangements for accomplishing the objectives of the patient interface assembly embodying the invention will be obvious for those skilled in the art. For instance the use of a connection member 8 can be combined with the use of any of the cheek mount support members 2 as described above, especially in combination with the cheek mount support members having a first and a second member which are surrounding the apex of the cheek bone as described in accordance with the first, third, and fourth embodiment.

It is to be understood that although preferred embodiments, specific constructions and configurations, as well as materials, have been discussed herein for devices according to the present invention, various changes or modifications in form and detail may be made without departing from the scope and spirit of this invention.

What is claimed is:

1. A patient interface assembly comprising:
   (a) a support member comprising a central support portion and a pair of cheek mount supports coupled to the central portion, each cheek mount support including a first end portion, a second end portion opposite the first end portion, a first member provided between the first end portion and the second end portion and a second member provided between the first end portion and the second end portion such that the first end portion, the second end portion, the first member, and the second member define a loop-shaped structure having an opening adapted to enable a peak portion of a cheekbone of a user to protrude through the opening responsive to the patient interface assembly being donned by the user, wherein the first end portion is spaced from the second end portion by a dimension D1, wherein the first member is spaced from the second member by dimension D2, wherein D1 is from 1 cm to 12 cm, and wherein D2 is from 1 cm to 8 cm;
   (b) a seal member operatively coupled to the support portion and being adapted to seal against a surface of the user to communicate a flow of gas with an airway of the user; and
   (c) an additional nasal support member comprising:
      (1) a first lateral side member having a first end operatively coupled to a first side of the central support portion, and (2) a second lateral side member having a first end operatively coupled to a second side of the central support portion, wherein at least a portion of the first lateral side member and the second lateral side member is rigid or semi rigid, wherein the additional nasal support member is structured such that no adhesive coupling between a bottom surface of the additional nasal support member and a face of the user exists when the patient interface assembly is worn by the user such that the additional nasal support member is structured to apply only pushing forces and not pulling forces on the face of the user when the patient interface assembly is worn by the user.

2. A patient interface assembly according to claim 1, wherein the additional nasal support member is adapted for applying a stabilizing force on the face of the user responsive to the patient interface assembly being worn by the user.

3. A patient interface assembly according to claim 2, wherein the additional nasal support member is configured for applying a stabilizing force which at least partially limits a force component exerted on a portion of the face of the user by the seal member responsive to the patient interface assembly being worn by the user, the stabilizing force acting between the patient interface assembly and the portion of the face of the user.

4. A patient interface assembly according to claim 2, wherein the additional nasal support member is directly coupled with the support member and comprises at least one discrete contact point with the user's face when the patient interface assembly is worn by the user, and wherein the additional nasal support member is adapted for not coming in contact with the user's face except for the at least one discrete contact point responsive to the patient interface assembly being worn by the user.

5. A patient interface assembly according to claim 2, wherein the additional nasal support member comprises two or three discrete contact points with the user's face when the patient interface assembly is worn by the user, and wherein the additional nasal support member is adapted for not coming in contact with the user's face except for the at least the two or three discrete contact points responsive to the patient interface assembly being worn by the user.

6. A patient interface assembly according to claim 1, wherein the additional nasal support member further comprises a connection member adapted for coupling a second end of the first lateral side member with a second end of the second lateral side member.

7. A patient interface assembly according to claim 1, wherein the first lateral side member has a second end opposite the first end of the first lateral side member, wherein the second lateral side member has a second end opposite the first end of the second lateral side member, wherein the second end of the first lateral side member is spaced from and not directly connected to the second end of the second lateral side member, and wherein the first end of the first lateral side member is connected to the first end of the second lateral side member by a connecting portion .

8. A patient interface assembly according to claim 7, wherein the first lateral side member is structured to rotate relative to a first one of the cheek mount supports about a first pivot member provided between the first lateral side member and the first one of the cheek mount supports, and wherein the second lateral side member is structured to rotate relative to a second one of the cheek mount supports about a second pivot member provided between the second lateral side member and the second one of the cheek mount supports.

9. The patient interface assembly according to claim 1, wherein the support member and the additional nasal support member are unitary.

10. The patient interface assembly according to claim 1, wherein the seal member is rotatably coupled to the support member.

11. A patient interface assembly according to claim 1, wherein D1 is from 2 cm to 10 cm, and wherein D2 is from 2 cm to 6 cm.

12. The patient interface assembly according to claim 1, further comprising a headgear assembly operatively coupled to the cheek mount supports.

* * * * *